US00PP24379P3

(12) United States Plant Patent
Smit

(10) Patent No.: US PP24,379 P3
(45) Date of Patent: Apr. 8, 2014

(54) ***PEPEROMIA* PLANT NAMED 'EDEN ROSSO'**

(50) Latin Name: *Peperomia marmorata×metallica*
Varietal Denomination: Eden Rosso

(76) Inventor: Obed Smit, Sappemeer (NL)

( * ) Notice: Subject to any disclaimer, the term of this patent is extended or adjusted under 35 U.S.C. 154(b) by 92 days.

(21) Appl. No.: 13/385,658

(22) Filed: Feb. 28, 2012

(65) Prior Publication Data

US 2013/0227753 P1 Aug. 29, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Peperomia* cultivar named 'Eden Rosso' is disclosed, characterized by unique, deeply veined foliage which is green and glossy on the upper surface, red on the under surface, with red petioles. Plants form strong rosettes. The new variety is a *Peperomia*, typically used as an ornamental plant.

2 Drawing Sheets

Figure 1:
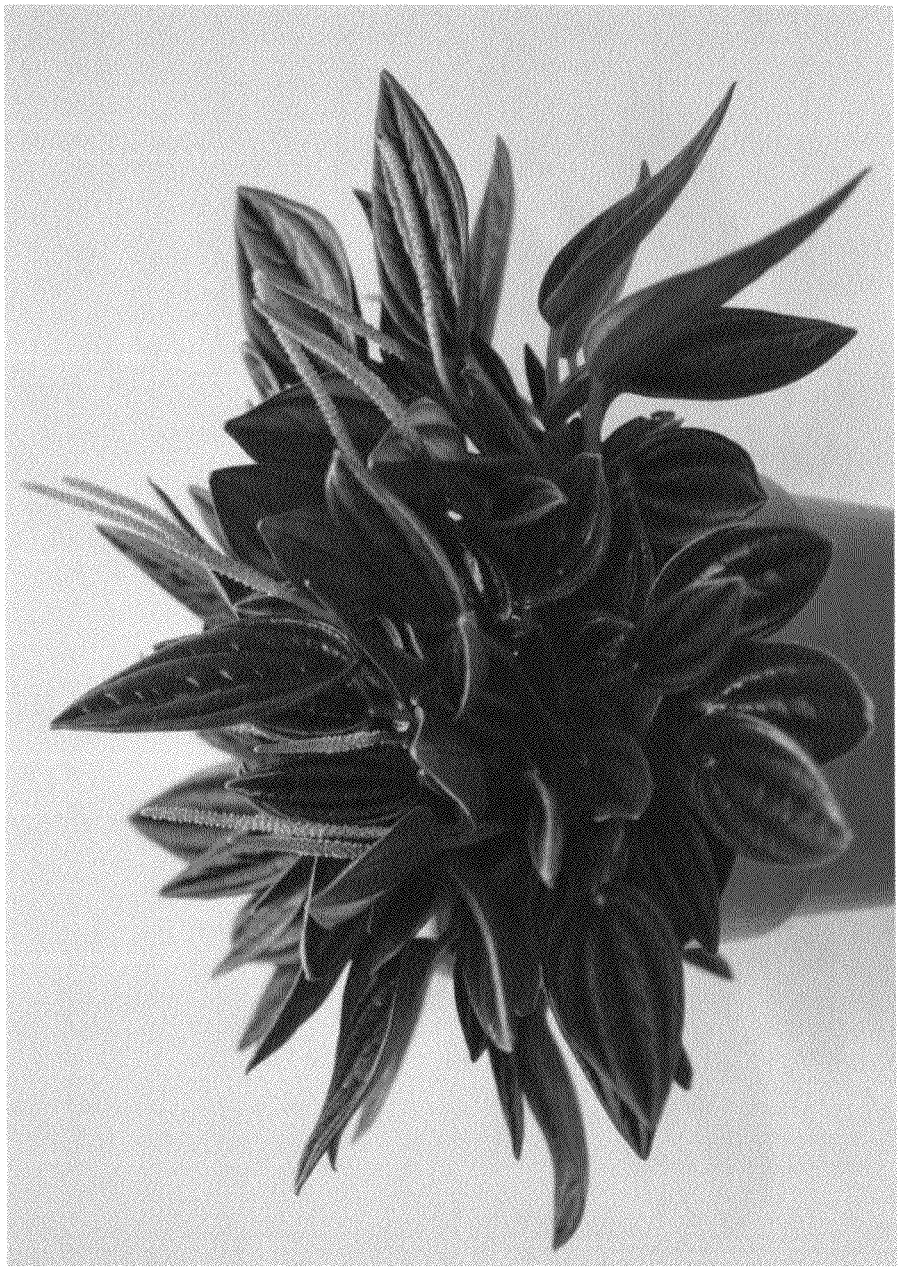

Latin name of the genus and species: *Peperomia marmorata×metallica.*

Variety denomination: 'Eden Rosso'.

BACKGROUND OF THE INVENTION

The new cultivar is a product of a planned breeding program. The new variety was selected as a seedling resulting from the crossing of the female parent, an unnamed, unpatented variety of *Peperomia marmorata* with the male parent, an unnamed, unpatented variety of *Peperomia metallica*. The crossing was made by the inventor, Obed J. Smit, a citizen of the Netherlands in June of 2010. 'Eden Rosso' was selected by the inventor in August of 2010 at a commercial greenhouse in Sappemeer, the Netherlands.

Asexual reproduction of the new cultivar 'Eden Rosso' by vegetative cuttings was first performed in Sappemeer, the Netherlands in September of 2010 and has shown that the unique features of this cultivar are stable and reproduced true to type through successive generations.

SUMMARY OF THE INVENTION

The cultivar 'Eden Rosso' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Eden Rosso' These characteristics in combination distinguish 'Eden Rosso' as a new and distinct *Peperomia* cultivar:

1. Upper side of leaf is glossy green.
2. Under side of leaf is red.
3. Petiole is red.
4. Deep veins, resulting in undulation along leaf blade.
5. Rosette-shaped growth.

Plants of the new cultivar 'Eden Rosso' are similar to plants of the female parent, *Peperomia marmorata* in most horticultural characteristics, however, plants of the new cultivar 'Eden Rosso' differ from *Peperomia marmorata* in the following characteristics:

1. Under side of leaf is less red in the seed parent.
2. Petioles are less red in the seed parent.
3. Leaf blade has a different shape than the seed parent.
4. Stronger growth than the seed parent.

Plants of the new cultivar 'Eden Rosso' are similar to plants of the male parent, *Peperomia metallica* in most horticultural characteristics, however, plants of the new cultivar 'Eden Rosso' differ from *Peperomia metallica* in the following characteristics:

1. Upper side of leaf blade is less green, more reddish in the pollen parent
2. The pollen parent does not form rosette type growth.
3. Different leaf blade shape and aspect.
4. Silver coloration around middle vein of leaf, characteristic of the pollen parent is not found in the new variety.

Plants of the new cultivar 'Eden Rosso' are similar to plants of the commercial variety *Peperomia caperata* 'Schumi Red', unpatented. However, plants of the new cultivar 'Eden Rosso' differ from 'Schumi Red' in the following characteristics:

1. 'Eden Rosso' upper leaf is green, compared to purple-red.
2. 'Eden Rosso' has less undulation between veins.
3. 'Eden Rosso' has an oblong, rather than heart shaped leaf.
4. 'Eden Rosso' has less depth of veins.
5. 'Eden Rosso' has red on the under side of leaf, rather than bronze-green.
6. 'Eden Rosso' has a red petiole, rather than bronze.

Plants of the new cultivar 'Eden Rosso' are similar to plants of the commercial variety *Peperomia obtusifolia*, unpatented. However, plants of the new cultivar 'Eden Rosso' differ in the following characteristics:

1. Different coloration of both upper and lower leaf blade.
2. 'Eden Rosso' has red petioles, rather than green.
3. 'Eden Rosso' has undulation between veins not found in *Peperomia obtusifolia.*

4. 'Eden Rosso' has an oblong, rather than round leaf shape.

BRIEF DESCRIPTION OF THE PHOTOGRAPHS

The accompanying photograph in FIG. 1 illustrates in full color a typical blooming plant of 'Eden Rosso' grown in a greenhouse. The plant is 13 weeks of age.

Figure 2:
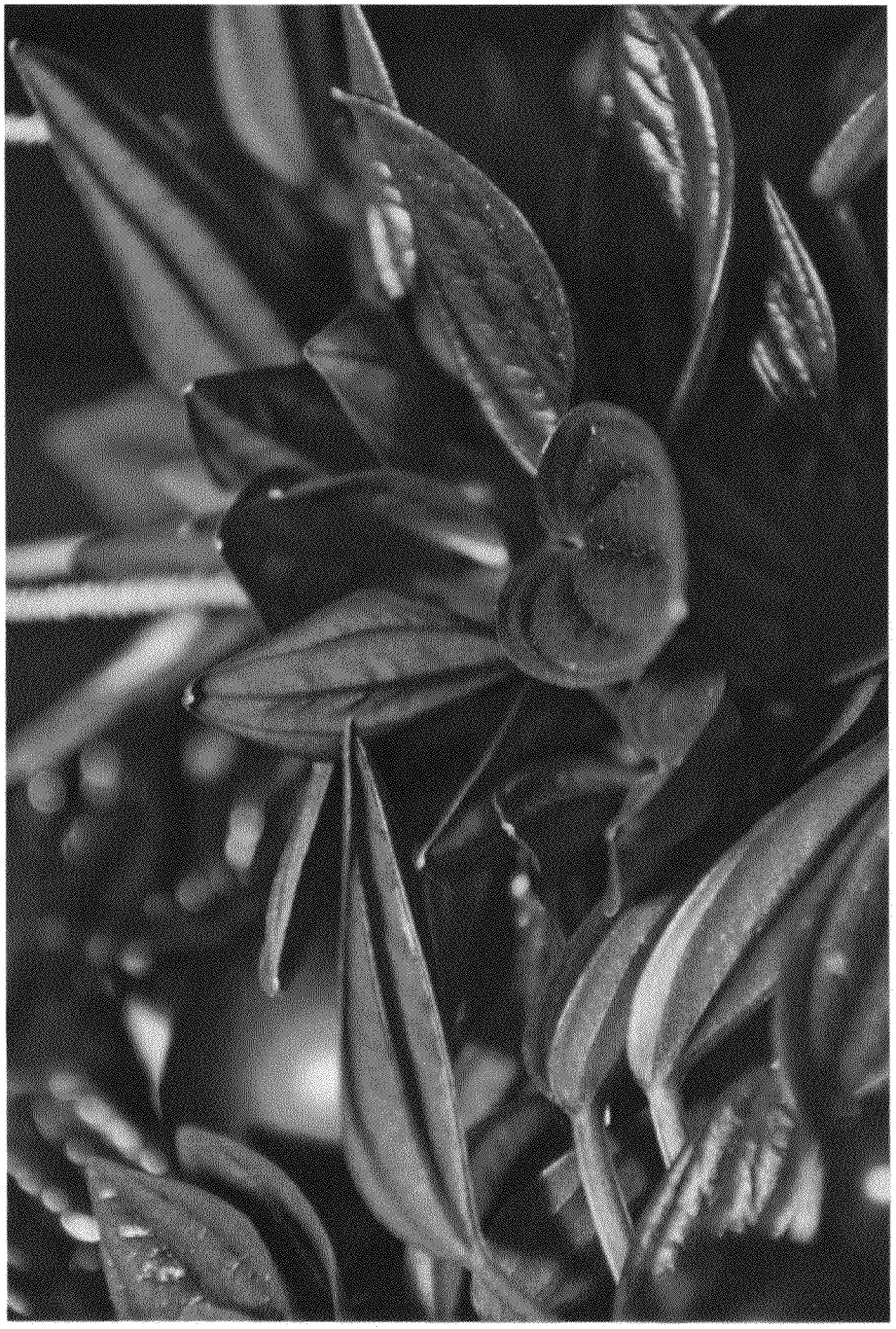

FIG. 2 illustrates a close up of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'Eden Rosso' plants grown in a greenhouse in Sappemeer, the Netherlands during the fall of 2011. The growing temperature ranged from 17° C. to 25° C. at night to 17° C. to 21° C. during the day. Measurements and numerical values represent averages of typical flowering types.

Botanical classification: *Peperomia marmorata×metallica* 'Eden Rosso'.

PROPAGATION

Time to initiate roots: About 21 days at approximately 20° C.
Time to produce a rooted cutting: About 84 days at 20° C.
Description of roots: Fibrous, fine.

PLANT

Plant spread: Approximately 14 cm.
Growth habit: Non-branching, rosetting.
Age of plant described: Approximately 13 weeks from a rooted cutting.

FOLIAGE

Leaf:
- *Arrangement.*—Rosette.
- *Quantity.*—Approximately 45.
- *Average length.*—Approximately 5 cm.
- *Average width.*—Approximately 1.5 cm.
- *Shape of blade.*—Ovate to oblong.
- *Apex.*—Acute.
- *Base.*—Rounded.
- *Margin.*—Entire.
- *Texture of top surface.*—Deep veins, undulation between veins, strong glossy appearance, glabrous.
- *Texture of bottom surface.*—Strong visible veins, glabrous.
- *Color.*—Young foliage upper side: Near RHS Green 137A, very shiny. Young foliage under side: Near RHS Red 53C. Mature foliage upper side: Near RHS Green 137A, very shiny. Mature foliage under side: Near RHS Red 53C.
- *Venation.*—Type: parallel. Venation color upper side: Near RHS Red 53A. Venation color under side: Near RHS Red 53A.
- *Petiole.*—Average Length: Approximately 3 cm. Diameter: Approximately 3 mm. Texture: glabrous. Strength: strong. Color: Near RHS Red 53A.

FLOWER

Natural flowering season: Short day blooming, normally blooms under daylength conditions of less than 12 hours of light.
Inflorescence type and habit: A spike containing both male and female flowers on same spike. No petals or sepals, highly reduced individual flowers.
Flower longevity on plant: 1 to 2 months.
Quantity of flowers: About 15 spikes plant, hundreds of minute flowers per spike.
Inflorescence size:
- *Diameter.*—Approximately 5 mm.
- *Height.*—Approximately 5 to 7 cm.

Individual flower size:
- *Diameter.*—Approximately 0.5 mm.
- *Height.*—Approximately 0.3 mm.

Bud:
- *Shape.*—Immature spike.
- *Length.*—Deviating with age, shorter than mature spike.
- *Diameter.*—Approximately 5 mm.
- *Color.*—Near RHS Yellow-Green 145A.

Petals: None.
Sepals: None.
Peduncle:
- *Length.*—3 to 4 cm.
- *Diameter.*—4 mm.
- *Color.*—Near RHS Red 45C.
- *Orientation.*—Straight, various angles.
- *Strength.*—Strong.
- *Texture.*—Glabrous.

REPRODUCTIVE ORGANS

Stamens:
- *Number.*—Immeasurable.
- *Filament length.*—Immeasurable.

Anthers:
- *Shape.*—Globular.
- *Length.*—Approximately 1 mm.
- *Color.*—Near RHS Green-White 157A.
- *Pollen.*—Color: Near RHS Green-White 157C. Quantity: Abundant.

Pistil:
- *Number.*—1 per flower.
- *Length.*—Approximately 1 mm.

OTHER CHARACTERISTICS

Seeds and fruits: Occasionally produces minute seeds, round, 1 to 2 mm, colored near Brown 200A.
Disease/pest resistance: Sensitive to *Rhizoctonia*.

What is claimed is:

1. A new and distinct cultivar of *Peperomia* plant named 'Eden Rosso' as herein illustrated and described.

* * * * *